(12) United States Patent
Li et al.

(10) Patent No.: US 11,479,534 B2
(45) Date of Patent: Oct. 25, 2022

(54) COMPOUND AND USE THEREOF IN MEDICINE

(71) Applicant: Changsha Hooz Bioscience And Technology Co., Ltd, Hunan (CN)

(72) Inventors: Xiong Li, Hunan (CN); Guojian Xie, Hunan (CN)

( * ) Notice: Subject to any disclaimer, the term of this patent is extended or adjusted under 35 U.S.C. 154(b) by 184 days.

(21) Appl. No.: 16/962,262

(22) PCT Filed: Dec. 5, 2018

(86) PCT No.: PCT/CN2018/119300
§ 371 (c)(1),
(2) Date: Jul. 15, 2020

(87) PCT Pub. No.: WO2019/141009
PCT Pub. Date: Jul. 25, 2019

(65) Prior Publication Data
US 2021/0061773 A1 Mar. 4, 2021

(30) Foreign Application Priority Data
Jan. 16, 2018 (CN) .......................... 201810038937.6

(51) Int. Cl.
*C07D 239/545* (2006.01)
*C07D 401/12* (2006.01)
*C07D 403/12* (2006.01)
*C07D 409/12* (2006.01)
*C07D 405/12* (2006.01)
*A61P 35/00* (2006.01)
*A61P 17/06* (2006.01)
*A61P 13/08* (2006.01)

(52) U.S. Cl.
CPC .......... *C07D 239/545* (2013.01); *A61P 35/00* (2018.01)

(58) Field of Classification Search
CPC ............. C07D 239/545; C07D 401/12; C07D 403/12; C07D 409/12; C07D 405/12; A61P 35/00; A61P 17/06; A61P 13/08
See application file for complete search history.

*Primary Examiner* — Bruck Kifle
(74) *Attorney, Agent, or Firm* — Prakash Nama; Global IP Services, PLLC (57) ABSTRACT

Disclosed are a compound and a pharmaceutically acceptable salt thereof, which can be used, by means of a chemical small molecule which targets both UHFR1 and HDAC1, or a pharmaceutically acceptable salt thereof, as corresponding inhibitors or drugs for treating diseases, and are used for treating myelodysplastic syndrome, psoriasis, scar hyperplasia, prostate or breast hyperplasia, hematologic neoplasms and solid cancers alone or combined with other methods. Same have a good therapeutic effect.

4 Claims, 7 Drawing Sheets

COMPOUND AND USE THEREOF IN MEDICINE

BACKGROUND OF THE INVENTION

The present invention relates to a kind of compound and its pharmaceutical use, and specifically relates to a small molecule compound dual-targeting UHRF1 and HDAC1.

HDAC family molecules and DNMT1 are important epigenetic regulatory molecules. Although they are highly expressed in several tumor tissues, they are also expressed in varying levels in different normal tissues and organs. HDAC inhibitors Vorinostat or Chidamide have been clinically shown to have relatively good therapeutic effects on cutaneous T-cell lymphoma, and DNMT1 inhibitors such as 5-azacitidine and decitabine have been clinically shown to have relatively good therapeutic effects on myelodysplastic syndrome. However, they have also shown various degrees of toxic side effects, so their use in treating solid tumors is limited. UHRF1 is an important gene that regulates DNA methylation in epigenetics, and is also involved in the regulation of DNA replication and repair of DNA damage, UHRF1 is also an oncogene, with low expression in normal tissues (5 to 70 times lower than HDAC1 and DNMT1), but high expression in many blood tumors and solid cancer tissues, making it an ideal target for anticancer drugs, UHRF1 knockdown by RNAi interference significantly reduces cell proliferation and promotes sensitivity of cells to radiochemotherapy. Therefore, effective small molecule compound targeting UHRF1 and HDAC1 can be developed and used solely or in combination with other methods to treat proliferative abnormalities and disorders, including but not limited to proliferative diseases such as myelodysplastic syndrome, psoriasis, scar hyperplasia, and prostatic hyperplasia or ductal hyperplasia, benign tumors, hematological tumors and solid cancers including types of cancers of neuroendocrine transformation.

BRIEF SUMMARY OF THE INVENTION

An object of the present invention is to provide a small molecule compound or its pharmaceutically acceptable salts dual-targeting UHRF1 and HDAC1 as a corresponding inhibitor or a drug that cures diseases, used solely or in combination with other methods to treat the aforementioned diseases and to increase the pharmaceutical effects of corresponding drugs.

The present invention provides a kind of compound and pharmaceutically acceptable salts thereof; the compound has the following formula:

wherein n is selected from a positive integer from 1 to 7, and R is selected from one of the following substituents: —H, —F, —Cl, —Br, —I, —NH2, —OH, —CN, —SH, —CF3, —CH3, —CH2CH3, In the above general formula, a change of R group can affect the solubility and crystallization of the compound.

Preferably, the compound has the following formula:

Preferably, the pharmaceutically acceptable salts are: chloride, bromide, iodide, phosphate, sulfate, carbonate, bicarbonate, formate, acetate, propionate, benzoate, picolinate, fumarate, maleate, malate, succinate, methanesulfonate, tosylate, trifluoromethanesulfonate, tetrafluoroborate or hexafluorosulfate.

The present invention also provides the use of said compound and pharmaceutically acceptable salts thereof in the preparation of treating (used solely or in combination with other methods of treatment) myelodysplastic syndrome, psoriasis, scar hyperplasia, prostatic hyperplasia, ductal hyperplasia, hematological tumors and tumors (mainly refer to solid cancers).

The present invention also provides the use of the above compound and pharmaceutically acceptable salts thereof in the preparation of UHRF1 and/or HDAC1 inhibitors.

Synthetic routes of the above compound are the same, where a value of n and the change of substituent R will not affect the synthesis routes. For example, compound has the following synthetic route:

The beneficial effect of the present invention is that the compound of the present invention and its pharmaceutically acceptable salts can simultaneously target UHRF1 and/or HDAC1 to prepare corresponding drugs. The present invention can be used solely or in combination with, other methods to treat diseases or disorders of proliferative abnormalities, including but not limited to proliferative diseases such as myelodysplastic syndrome, psoriasis, scar hyperplasia, prostate hyperplasia and ductal hyperplasia, benign tumors, hematological tumors and solid cancers, and can obtain a good therapeutic result.

BRIEF DESCRIPTION OF THE DRAWINGS

FIG. 2a, FIG. 2b, FIG. 2c, FIG. 2d show the IC50 values of the compound of the present invention for selectively killing different cancer cells, wherein FIG. 2a shows the results for RWPE1 cells, FIG. 2b shows the results for HPrEC cells, FIG. 2c shows the results for PC3 cells, and FIG. 2d shows the results for DU145 cells.

FIG. A, FIG. 58, FIG. 5C and FIG. 5D show the effects of compound M3 on weight, heart function, liver function and kidney function of nude mouse respectively.

DETAILED DESCRIPTION OF THE INVENTION

The present invention will be further described below with reference to some embodiments

Embodiment 1: Synthesis of Compound M3

Synthetic route is as follows:

1. Synthesis of suberic anhydride: adding suberic acid (5.0 g, 28.7 mmol) to 10 mL of acetic anhydride, heating and stirring and refluxing for 1 h, and then cooling to room temperature, next, distilling off the solvent under reduced pressure to obtain a yellow solid, recrystallizing the yellow solid using acetonitrile to obtain a white solid of 4.3 g (96% yield rate). 1HNMR (400 MHz, CDCl3): δ 2.41 (m, 4H), 1.62 (m, 4H), 1.34 (n, 4H).

2. Synthesis of 8-((2,4-dioxo-1,2,3,4-tetrahydropyrimidin-1-yl)amino)-8-oxooctanoic acid: dissolving dianhydride (1.6 g, 10.0 mmol) using 20 mL of TH, stirring under ice bath while adding in aminouracil (1.3 g, 10.0 mmol), and then stirring under room temperature for 30 min to obtain a mixture, diluting the mixture with water to obtain a white solid through precipitation, filtering and collecting the white solid, recrystallizing using water to obtain a final white solid of 2.7 g (96% yield rate). 1HNMR (400 MHz, DMSO): δ 12.05 (br, 1H), 11.47 (br, 1H), 10.66 (s, 1H), 9.07 (s, 1H), 8.09 (s, 1H), 8.06 (s, 1H), 2.32-2.35 (m, 2H), 1.94-1.96 (m, 2H), 1.47-1.52 (n, 4H), 1.26-1.29 (m, 4H).

Figure 4:
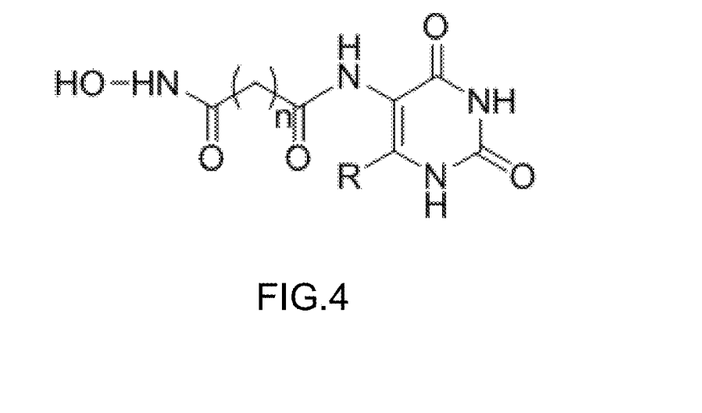
FIG. 4 is a chemical formula showing the structure of compound M3 of the present invention.

3. Synthesis of N1-(carbonyl-5-aminouracil)-N8-octylhydroxyamide: dissolving 8-((2,4-dioxo-1,2,3,4-tetrahydropyrimidin-5-yl)amino)-8-oxooctanoic acid (1.4 g, 5.0 mmol) in 20 mL of anhydrous THF, maintaining the temperature at 0° C., and then adding in ethyl chloroformate (600 mg, 6.0 mmol) and triethylamine (0.7 mL) to obtain a mixture, stirring the mixture for 10 min, and then filtering out a resulting solid to obtain a filtrate, adding the filtrate in a freshly prepared solution of hydroxylamine in methanol (170 mg in 2 mL, 5.0 mmol) to obtain a reaction solution, and then stirring the reaction solution under room temperature for 15 min, distilling off the solvent, and recrystallizing a residue using acetonitrile to obtain a white solid of 890 mg (60% yield rate). ESI-MS: [M+H]+=299.10; 1HNMR (400 MHz DMSO): δ 11.41 (br, 1H), 10.65 (br, 1H), 10.37 (s, 1H), 906 (s, 1H), 8.68 (s, 1H), 806 (s, 1H), 2.33-2.35 (m, 2H), 1.94 (t, J=8.0 Hz, 2H), 1.46-1.52 (m, 4H), 1.22-1.52 (m, 4H). The above data of the characterizing structures of said compound M3 confirms the illustrative structure of said compound M3 as shown in FIG. 4.

Embodiment 2: Biological Activity Tests

Conditions of the Experiments:

Prostate cancer cells and a prostate-cancer-cell-induced xenograft tumor model are used to detect the molecular targeting effect of compound M3 of the present invention on UHRF1 and HDAC1, and the effect of different concentrations of said compound M3 of the present invention on the proliferation of prostate cancer cells and control normal cells, so as to evaluate the anti-cancer activity of said compound M3 in vitro, predict the safety of said compound M3, and test the effect of oral administration of said compound M3 on the growth of prostate cancer xenograft in nude mouse. In order to better evaluate the pharmaceutical efficacy and safety of said compound M3 of the present invention, a UHRF1 small molecule inhibitor NSC232003 published in the European Journal of Medicinal Chemistry, 114:390-396, 2016 is used as a control and being referred to as compound M1 in the figures and in the experimental data below.

Experimental Results:

1. Targeting Performance of Compound M3 on UHRF1 and HDAC1 Molecules.

Figure 1:
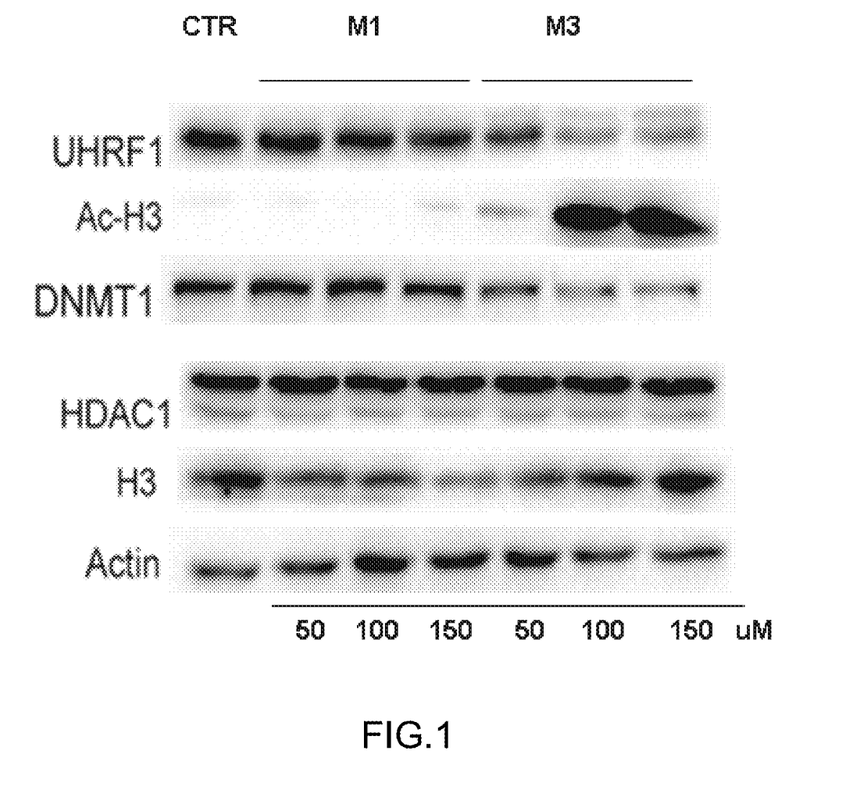
FIG. 1 is an experimental result of targeting performance of a control medical compound M1 (a published UHRF1 small molecule inhibitor NSC232003, published in European Journal of Medicinal Chemistry, 114: 390-396, 2016) and the compound M3 prepared according to embodiment 1 of the present invention in different dosages.
Figure 2A:
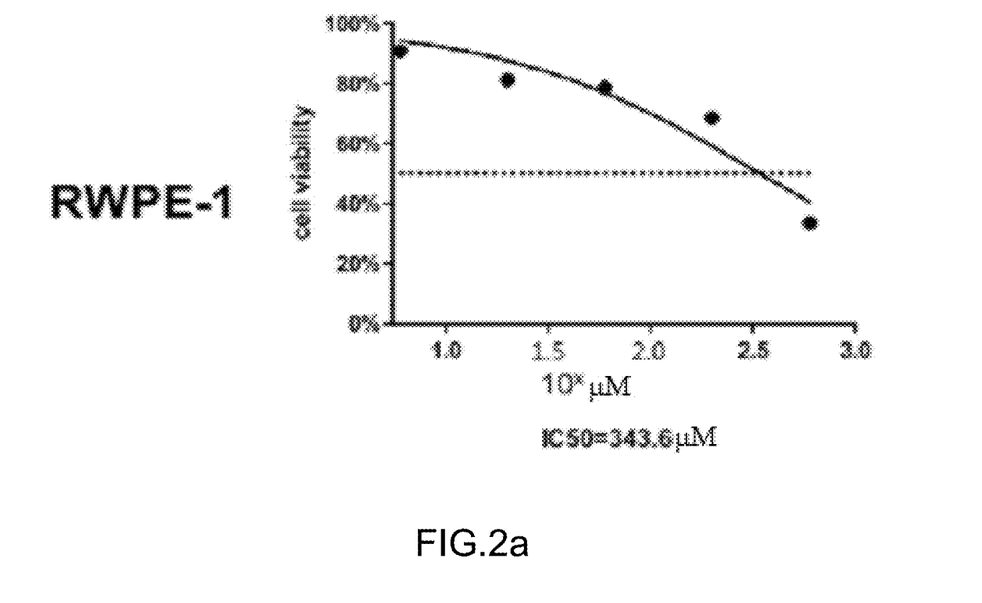
Figure 2B:
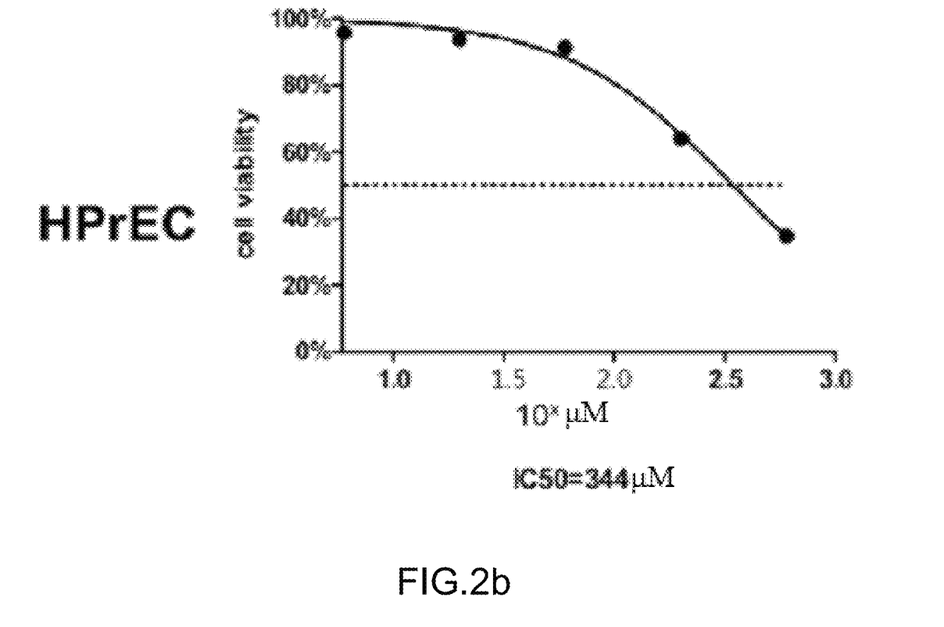
Figure 2C:
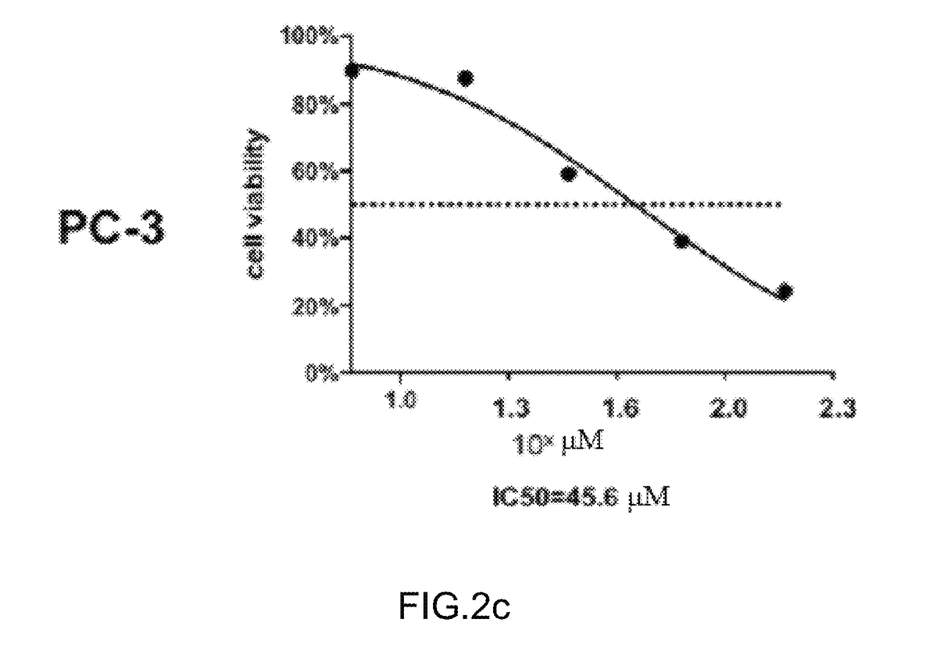
Figure 2D:
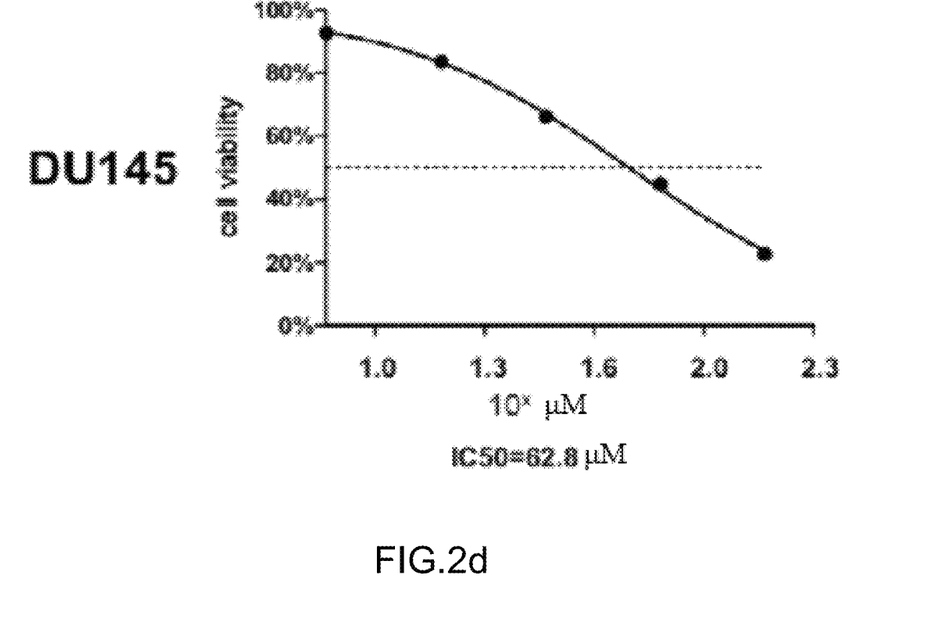

Culturing a same amount of prostate cancer cell line DU145 in each well of a 6-well culture dish, allowing cell adhesion for 24 hours, and then using different doses of said compound M3 (50, 100 and 150 μM) to treat the prostate cancer cell DU145, and using said compound M1 as a control drug. After 24 hours, harvest the cells for Western blot to detect the protein levels of UHRF1, histone H3 and acetylated histone H3. The results show that compound M3 of the present invention specifically reduces the protein level of the oncogene UHRF1 in prostate cancer cells in a dose-dependent manner, and causes an increase in acetylation level of histone H3, however, the total histone H3 level is not affected. Since said compound M3 has a dual targeting effect on UHRF1 and HDAC, protein expression of their common downstream gene DNMT1 is significantly reduced (FIG. 1). The results of this experiment verifies that the compound M3 of the present invention specifically dual-targeting UHRF1 and HDAC molecules.

2. Said Compound M3 Kills Prostate Cancer Cells in a Dose-Dependent Manner, but has Low Toxicity to Normal Cells.

Culturing prostate cancer cells PC3 and DU145 cells, as well as non-cancerous normal cells (5000 cells/well) in a 96-well cell culture dish, and then using different doses of said compound M3 to treat prostate cancer cells PC3 and DU145 cells and normal prostate cancer cells RWPE1 and HPrEC. After 72 hours, detecting the survival rate of the cells by MTS method, and calculate 150 values of said compound M3 for different cells using software.

The results show that said compound M3 manifests obvious cytotoxicity to prostate cancer cells PC3 and DU145, with its half inhibitory dose (IC50) less than 50 μM for both PC3 and DU145. However, IC50 of said compound M3 for normal prostate cancer epithelial cells RWPE1 and HPrEC is significantly increased, which is greater than 300 μM for both RWPE1 and HPrEC. Through comparison, said compound M3 of the present invention has a good selectivity for killing prostate cancer cells. (FIG. 2a-FIG. 2d)

3. Said Compound M3 has an Obvious Inhibitory Effect on the Growth of Prostate Cancer Xenograft Tumor on Nude Mouse.

Establishing a subcutaneous xenograft model of prostate cancer DU145 cells (1×106) in immunodeficient mouse by subcutaneous injection, allowing around 2-3 weeks for the xenograft to grow into a size of around 250 mm3, and then intragastrically administering the compound M3 of the present invention (100 mg/kg/day) once a day, 5 days a week with 2 days rest in between, for a total of 4 weeks of continuous treatment. Said compound M and solvent DMSO are used as controls. Tumor size is measured before treatment and every 3 days after treatment begins. The size of the tumor is calculated according to the formula V=length× width 2/2.

Figure 3A:
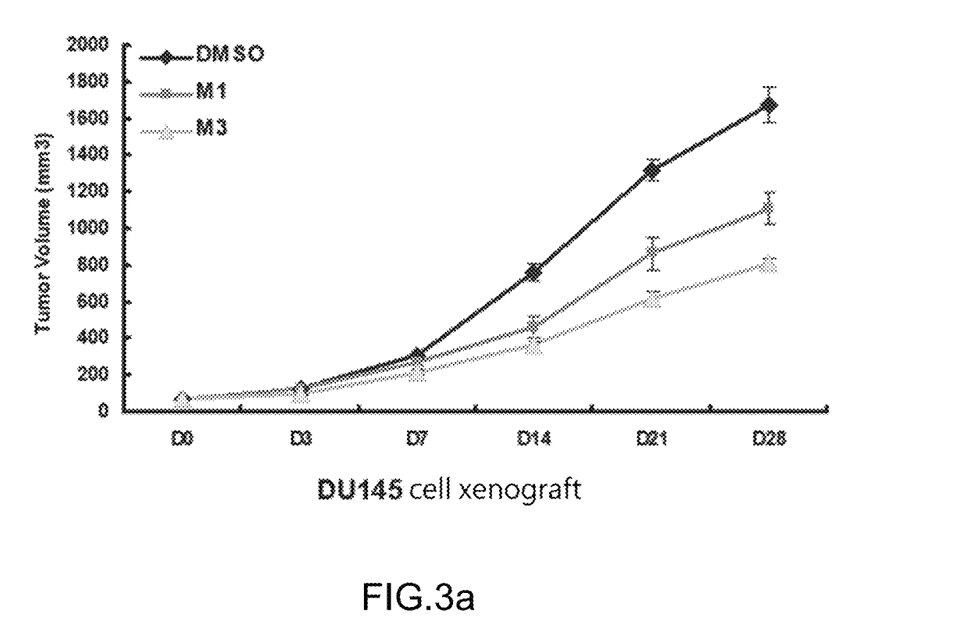
FIG. 3a and FIG. 3b are charts showing growth inhibition effect of xenograft tumor of prostate cancer on nude mouse under the use of different compounds M1 and M3 as well as different dosages of compound M3.
Figure 3B:
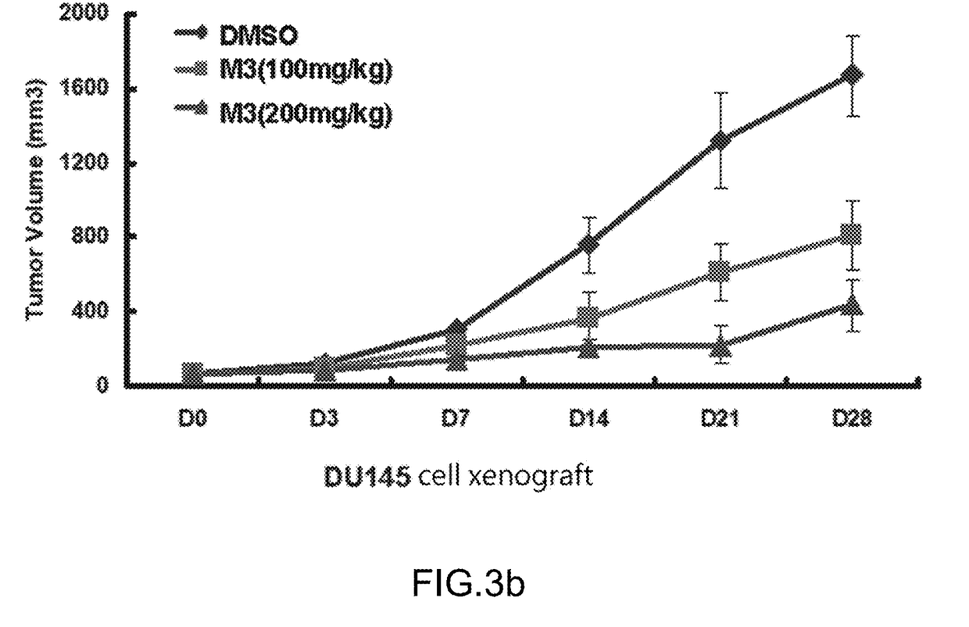

The results show that in the xenograft tumor model established for prostate cancer cell DU145, the compound M3 of the present invention according to embodiment 1 significantly reduces tumor growth compared with the control compound M1. (FIG. 3a and FIG. 3b) The compound M3 of the present invention manifests very obvious antitumor activity.

Experimental conclusion: In vitro cell experiments and animal experiment confirm that said compound M3 of the present invention has a very good targeting effect on UHRF1 and HDAC1 molecules, has a very specific killing effect on prostate cancer cell, and manifests obvious inhibition on the growth of prostate cancer xenograft tumor in nude mouse.

4. Said Compound M3 is Obviously Safe.

Intragastrically administering the compound M3 of the present invention (200 mg/kg/day) in an immunodeficient nude mouse once a day, 5 days a week with 2 days rest in between, for a total of 4 weeks of continuous treatment; using solvent DMSO as a control. Weight of the nude mouse is measured before treatment and every 3 days after the treatment begins. When the experiment ends, extract blood from the nude mouse, separate blood serum, and detect the changes in biochemical indicators, including: aspartate aminotransferase (AST) and alanine aminotransferase (ALT) indicative of liver function, blood urea nitrogen (BUN) and creatinine (CREA) indicative of kidney function, and creatine kinase (CK) and 1 lactate dehydrogenase (LDH-L) indicative of heart function, to evaluate the effect of compound M on heart, liver and kidney functions.

Figure 5A:
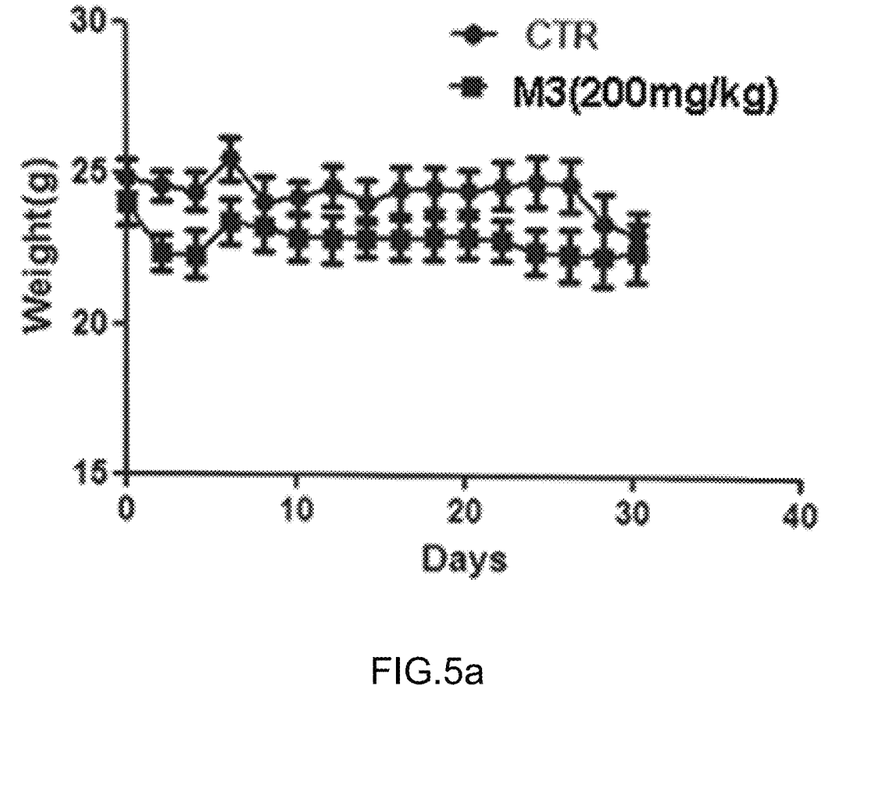
Figure 5B:
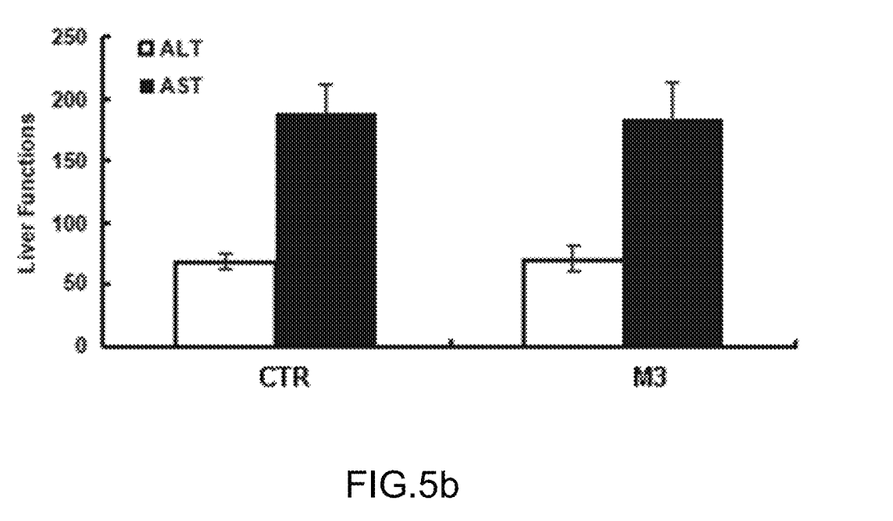
Figure 5C:
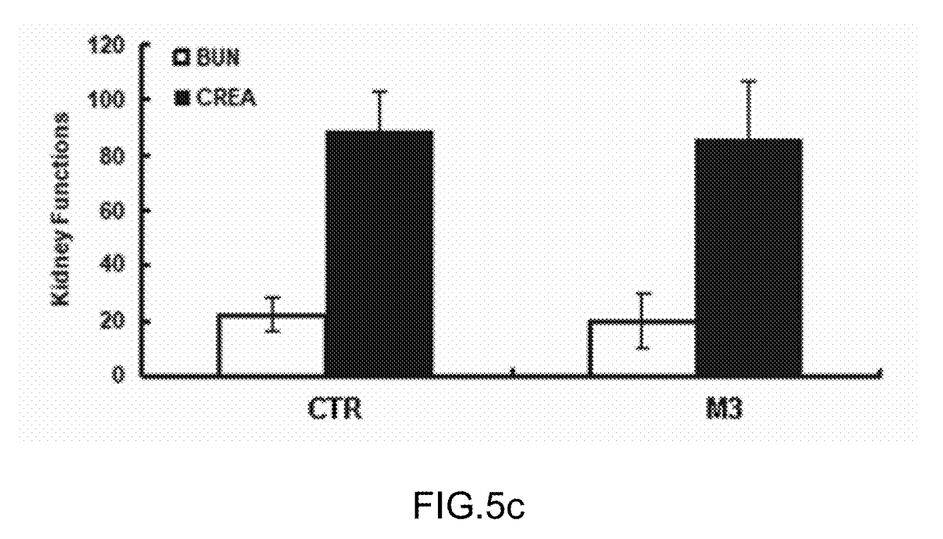
Figure 5D:
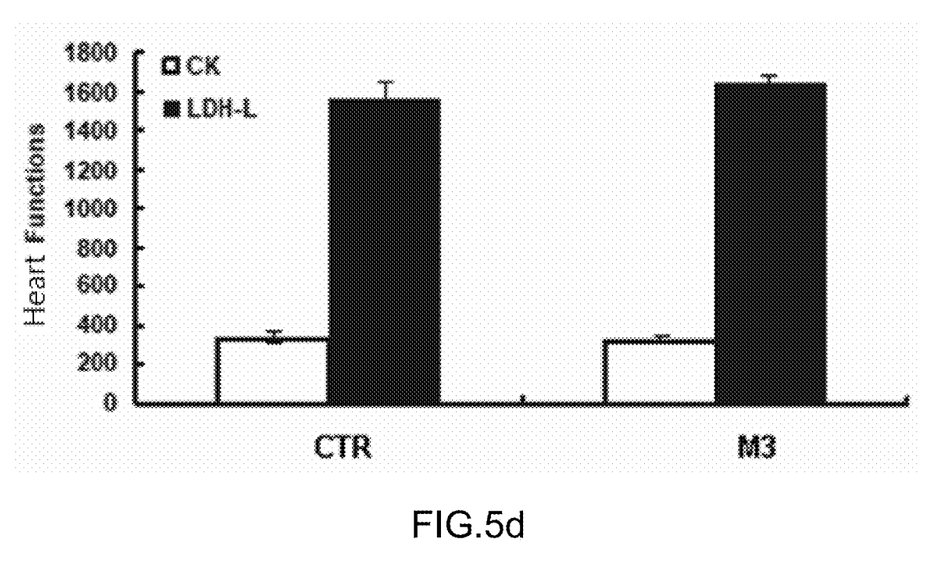

The results show that said compound M3 according to embodiment 1 of the present invention (dose of 200 mg/kg/day) does not significantly reduce the weight of the nude mouse (FIG. 5a), also, there is no significant effect on liver, kidney and heart functions (FIGS. 5b, c and 5d).

Experimental conclusion: In vitro cell experiments and animal experiment confirm that said compound M3 of the present invention is obviously safe.

Embodiment 3: Comparative experiments between said compound M3 and derivatives with similar structures Derivatives with similar structures can be obtained by the same preparation methods according to the above embodiments, including:

Compared with said compound M3, these derivatives are different in the lengths of their side chains. However, according to preliminary experimental discoveries, drug activities of these derivatives are not satisfactory in the same model used in the present invention, meaning that lengths of the side chains have greater impact on drug activities.

Figure 6:
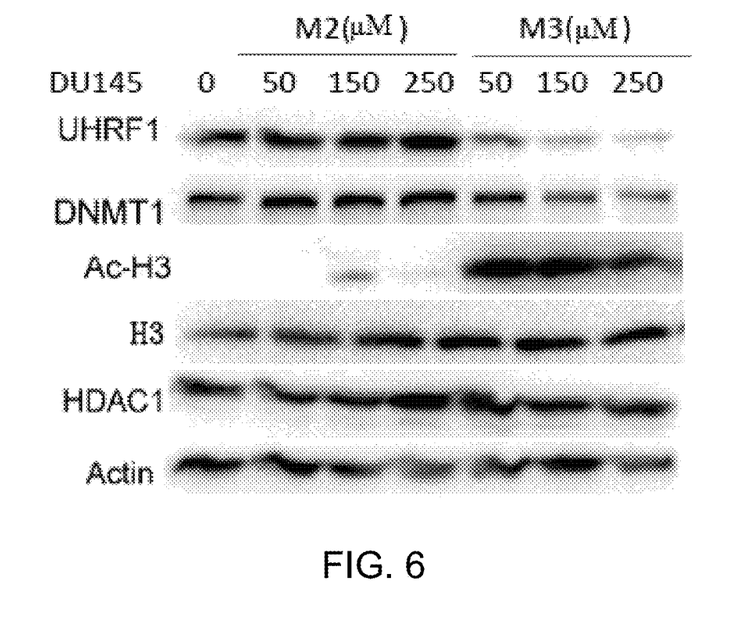
FIG. 6 is an experimental results showing the targeting performance of compound M2 arid said compound M3 according to embodiment 1 of the present invention.

As shown in FIG. 6, said compound M2 does not have any impact on the protein level of UHRF1 target. Under the same dose, said compound M3 significantly reduces the protein stability of UHRF1; likewise, said compound M2 has no obvious impact on the activity of HDAC1, but said compound M3 significantly inhibits the activity of HDAC1 (shown as significant increase in acetylated histone H3).

What is claimed is:
1. A compound of formula:

or a pharmaceutically acceptable salt thereof;
wherein n is selected from a positive integer from 1 to 7, and R is selected from the group consisting of —H, —F, —Cl, —Br, —I, —NH$_2$, —OH, —CN, —SH, —CF$_3$, —CH$_3$, —CH$_2$CH$_3$, -continued 2. The compound according to claim 1, which is or a pharmaceutically acceptable salt thereof.

3. The compound or pharmaceutically acceptable salt thereof according to claim 1, wherein the salt is selected from the group consisting of chloride, bromide, iodide, phosphate, sulfate, carbonate, bicarbonate, formate, acetate, propionate, benzoate, picolinate, fumarate, maleate, malate, succinate, methanesulfonate, tosylate, trifluoromethanesulfonate, tetrafluoroborate and hexafluorosulfte.

4. The compound or pharmaceutically acceptable salt thereof according to claim 2, wherein the salt is selected from the group consisting of chloride, bromide, iodide, phosphate, sulfate, carbonate, bicarbonate, formate, acetate, propionate, benzoate, picolinate, fumarate, maleate, malate, succinate, methanesulfonate, tosylate, trifluoromethanesulfonate, tetrafluoroborate and hexafluorosulfte.

* * * * *